(12) United States Patent
Huber et al.

(10) Patent No.: US 9,376,451 B1
(45) Date of Patent: Jun. 28, 2016

(54) METHOD FOR SELECTIVELY PREPARING EVOGLUCOSENONE (LGO) AND OTHER ANHYDROSUGARS FROM BIOMASS IN POLAR APROTIC SOLVENTS

(71) Applicant: Wisconsin Alumni Research Foundation, Madison, WI (US)

(72) Inventors: George W. Huber, Middleton, WI (US); Fei Cao, Nanjing (CN); James A. Dumesic, Verona, WI (US); Thomas J. Schwartz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/588,178

(22) Filed: Dec. 31, 2014

(51) Int. Cl.
*C07D 493/08* (2006.01)

(52) U.S. Cl.
CPC .................................... *C07D 493/08* (2013.01)

(58) Field of Classification Search
USPC .......................................................... 549/397
See application file for complete search history.

(56) References Cited

U.S. PATENT DOCUMENTS

| 2013/0172578 A1 | 7/2013 | Allgeier et al. |
| 2013/0231505 A1 | 9/2013 | Allgeier et al. |

FOREIGN PATENT DOCUMENTS

WO WO 2013/101980 A1 7/2013

OTHER PUBLICATIONS

Dobele, G. et al., Pre-treatment of biomass with phosphoric acid prior to fast pyrolysis a Promising method for obtaiing 1,6-anhdrosaccharides in high yields, *Journal of Analytical and Applied Pyrolysis* 2003, 68-9, 197-211.
Kudo, S. et al., Efficient levoglusocesnone production by catalytic pyrolysis of cellulose mixed with ionic liquid, *Green Chemistry* 2011, 13, 3306-3311.
Kudo, S. et al., Sulfonate Ionic Liquid as a Stable and Active Catalyst for Levoglucosenone Production from Saccharides via Catalytic Pyrolysis, *Catalysts* 2013, 3, 757-773.
Lu, Q. et al., Influence of pyrolysis temperature and time on the cellulose fast pyrolysis products: Analytical Py-GC/MS study, *Journal of Analytical and Applied Pyrolysis* 2011, 92, 430-438.
Lu, Q. et al., Catalytic Fast Pyrolysis of Cellulose Mixed With Sulfated Titania to Produce Levoglucosenone: analytical PY-GC/MS Study, *Bioresources* 2012, 7, 2820-2834.
Miura, M. et al., Microwave pyrolysis of cellulosic materials for the production of anhydrosugars, *Journal of Wood Science* 2001, 47, 502-506.
Muller et al., Design, Synthesis, and Biological Evaluation of Levoglucosenone-Derived Ras Activation Inhibitors, *ChemMedChem* 2009 4(4): 524-528.
Ostermeier et al., Total synthesis of (+)-chloriolide, J. Org. Chem. B 2014, 79(9):4038-42.
Sarotti, A.M. et al., An efficient microwave-assisted green transformation of cellulose into levoglucosenone. Advantages of the use of an experimental design approach, *Green Chemistry* 2007, 9, 1137-1140.
Sarotti et al., Recent Applications of Levoglucosenone as Chiral Synthon, *Current Organic Synthesis* 2012, 9:439-459.
Shafizadeh, et al., Some reactions of levoglucosenone, *Carbohydr. Res.* 1979, 71:169-191.
Sherwood et al., Dihydrolevoglucosenone (Cyrene) as a bio-based alternative for dipolar aprotic solvents, *Chem. Commun.*, 2014, 50:9650-9652.
Sui, X-w. et al., Preparation of levoglucosenone through sulfuric acid promoted pyrolysis of bagasse at low temperature, *Bioresource Technology* 2012, 103, 466-469.
Wei, X. et al., Fast pyrolysis of cellulose with solid acid catalysts for levoglucosenone, *Journal of Analytical and Applied Pyrolysis* 2014, 107, 150-154.
Zandersons, J. et al., Feasibility of broadening the feedstock choice for levoglucosenone production by acid pre-treatment of wood and catalytic pyrolysis of the obtained lignocellulose, *Journal of Analytical and Applied Pyrolysis* 2013, 103, 222-226.

*Primary Examiner* — Kristin Vajda
(74) *Attorney, Agent, or Firm* — Joseph T. Leone, Esq.; DeWitt Ross & Stevens S.C.

(57) ABSTRACT

A method to produce 5-hydroxymethylfurfural (HMF) is described in which a reactant including cellulose, lignocellulose, or a combination thereof, in a reaction mixture of a polar, aprotic solvent and an acid is reacted for a time, at a temperature, and at a hydrogen ion concentration wherein at least a portion of the cellulose or lignocellulose present in the reactant is converted to HMF. The reaction mixture is initially substantially devoid of water. As the reaction proceeds, dehydration of intermediates causes the water concentration in the reaction mixture to rise to no more than about 2.0 wt % water.

27 Claims, 13 Drawing Sheets

METHOD FOR SELECTIVELY PREPARING EVOGLUCOSENONE (LGO) AND OTHER ANHYDROSUGARS FROM BIOMASS IN POLAR APROTIC SOLVENTS

FEDERAL FUNDING STATEMENT

This invention was made with government support under DE-FC02-07EF64494 awarded by the US Department of Energy. The government has certain rights in the invention.

BACKGROUND

Levoglucosenone (LGO; CAS No. 37112-31-5; systematic name (1S,5R)-6,8-dioxabicyclo[3.2.1]oct-2-en-4-one or 1,6-anhydro-3,4-dideoxy-β-D-glycero-hex-3-enopyranos-2-ulose) is an alternative, non-petroleum precursor which can be used as a building block chemical for producing various high-volume and value-added organic chemicals. LGO is notable for its highly functionalized, bicyclic structure which contains a chiral carbon, a double bond conjugated to a ketone, a protected aldehyde group, and two protected hydroxyl groups:

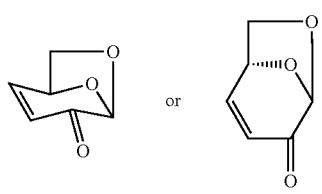

Levoglucosenone (LGO)

LGO is a highly dehydrated sugar that is conventionally derived from cellulose. It is a valuable intermediate in the synthesis of biologically active compounds, chiral therapeutic agents, and other value-added compounds. For a recent review of LGO as a chiral synthon, see Sarotti, Zanardi, Spanevello and Suárez (2012) "Recent Applications of Levoglucosenone as Chiral Synthon," *Current Organic Synthesis* 9:439-459.

Conventionally, LGO is made via pyrolysis of cellulose-containing materials such as waste paper. See, for example, Shafizadeh, Furneaux, and Stevenson, (1979) "Some reactions of levoglucosenone," *Carbohydr. Res.* 71:169-191. Yields, however, are quite low. The use of ionic liquids as solvents for LGO production has been proposed due to the solvation capabilities of the ionic liquids. However, significant challenges hinder the industrial use of ionic liquids for producing LGO. For example, due to the high cost of the ionic liquid solvent, the solvent must be quantitatively recovered and recycled to make the process economically attractive. The relatively low cellulose solubility (10-15 wt %) in ionic liquids, as well as the high viscosity and high toxicity of ionic liquids are also impeding factors. A number of routes to fabricate LGO are described in the prior art. These routes are summarized in Table 1:

TABLE 1

Summary of Conventional LGO Fabrication Routes

| Method | Catalyst | Temp (°C.) | Feed scale (g) | T (min) | Yield LGO (%) | Ref |
|---|---|---|---|---|---|---|
| Catalytic fast pyrolysis | $SO_4^{2-}/ZrO_2$ | 335 | 3 | 15 | 7.2-8.4 | 1 |
| | $H_2SO_4$ | 270 | 3 | 10 | 7.58 | 2 |
| | Zeolite | 550 | 1 | 5 | trace | 3 |
| | $H_2SO_4, H_3PO_4,$ $(NH_4)_2SO_4,$ $ZnCl_2,$ $Fe_2(SO_4)_3$ | 523 | | | 4.8 | 3 |
| Py-GC-MS | $H_3PO_4$ | 375 | 0.002 | 10 | 29-30[a] | 5 |
| | $H_3PO_4/(NH_4)_3PO_4$ | 900 | 0.01 | 15 | 50[b] | 6 |
| | Zeolites | 500 | 0.005 | 1 | 1.7 | 7 |
| | $H_3PO_4/Fe^{3+}$ | 500 | $5 \times 10^{-5}$ | | 30-40[a] | 8 |
| Ionic liquid | [EMIM] $CH_3C_6H_4SO_3$ | 300 | 0.05 | 20 | 11.5 | 9 |
| | [C_4(mim)_2] Cl_2 | 180 | 1 | 20 | 5.5 | 10 |
| Sulfolane | $H_2SO_4, H_3PO_4$ | 240-300 | 0.05 | 4 | 42.2 | 11 |

[a]Relative percent in bio-oil;
[b]Peak area percent.

Table 1 References

1. Q. Lu, X.-M. Zhang, Z.-B. Zhang, Y. Zhang, X.-F. Zhu, C.-Q. Dong, *Bioresources* 2012, 7, 2820-2834.
2. X. Wei, Z. Wang, Y. Wu, Z. Yu, J. Jin, K. Wu, *Journal Of Analytical And Applied Pyrolysis* 2014, 107, 150-154.
3. J. Zandersons, A. Zhurinsh, G. Dobele, V. Jurkjane, J. Rizhikovs, B. Spince, A. Pazhe, *Journal Of Analytical And Applied Pyrolysis* 2013, 103, 222-226.
4. X.-w. Sui, Z. Wang, B. Liao, Y. Zhang, Q.-x. Guo, *Bioresource Technology* 2012, 103, 466-469.
5. Q. Lu, X.-c. Yang, C.-q. Dong, Z.-f. Zhang, X.-m. Zhang, X.-f. Zhu, *Journal Of Analytical And Applied Pyrolysis* 2011, 92, 430-438.
6. J. A. Marshall, Iowa State University, 2008.
7. A. M. Sarotti, R. A. Spanevello, A. G. Suarez, *Green Chemistry* 2007, 9, 1137-1140.
8. G. Dobele, T. Dizhbite, G. Rossinskaja, G. Telysheva, D. Mier, S. Radtke, O. Faix, *Journal Of Analytical And Applied Pyrolysis* 2003, 68-9, 197-211.
9. M. Miura, H. Kaga, T. Yoshida, K. Ando, *Journal Of Wood Science* 2001, 47, 502-506.
10. S. Kudo, Z. Zhou, K. Norinaga, J.-i. Hayashi, *Green Chemistry* 2011, 13, 3306-3311.
11. S. Kudo, Z. Zhou, K. Yamasaki, K. Norinaga, J.-i. Hayashi, *Catalysts* 2013, 3, 757-773.

LGO is used (or can be used) in a wide range of industrial processes. For example, LGO can be converted to 1,6-hexandiol, which is used as a monomer for polyurethanes and polyesters:

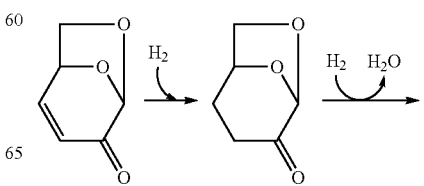

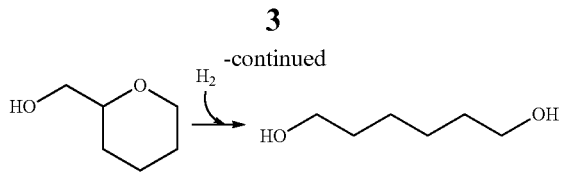

1,6-Hexandiol can be produced in 69% yield by the aqueous-phase hydrogenation of LGO using Pt/C and Pt/W/TiO$_2$. See Allgeier et al. WO 2013/101980, US 2013/0172578, and US 2013/0231505.

Levoglucosenone is also used to make dihydrolevoglucosenone, a solvent marketed as "Cyrene"-brand solvent (Circa Group Pty Ltd, Coburg North, Victoria, Australia.) It has solvent properties similar to commonly used dipolar solvents such as N-methyl-2-pyrrolidone, sulfolane, and dimethylsulfoxide. See Sherwood et al. (2014) "Dihydrolevoglucosenone (Cyrene) as a bio-based alternative for dipolar aprotic solvents," *Chem. Commun.,* 50:9650-9652. LGO has been used as a building block for syntheizing Ras activation inhibitors (a type of signal transduction inhibitor). See Muller et al. (2009) "Design, Synthesis, and Biological Evaluation of Levoglucosenone-Derived Ras Activation Inhibitors," *Chem Med Chem* 4(4): 524-528. LGO has also been used to make macrolide anti-microbials. See Ostermeier and Schobert (2014) "Total synthesis of (+)-chloriolide," J. Org. Chem. 79(9):4038-42. These various transformations are depicted in Scheme 1:

detectable products at 375° C. Zandersons et al. (2013) *Journal Of Analytical And Applied Pyrolysis* 103:222-226. Zhang and coworkers explored sulfated zirconia, a solid superacid, as a means to improve the yield of LGO, but their best yield was only 8/1%. Sui et al. (2012) *Bioresource Technology* 103:466-469. These low yields make it difficult to recover LGO from bio oil and have so far limited the large-scale exploitation of LGO.

Because of its wide industrial applicability, there remains a long-felt and unmet need for an easy, fast, and economical method to produce LGO from biomass.

SUMMARY OF THE INVENTION

Disclosed and claimed herein is a novel method to produce LGO from cellulosic biomass under mild reaction conditions in polar aprotic solvents (e.g., tetrahydrofuran), optionally without the presence of water (or very low concentrations of water). Preferred reaction temperatures are in the range of from about 80° C. to about 500° C., more preferably from about 80° C. to about 400° C., more preferably still from about 80° C. to about 300° C., and most preferably from about 140° C. to about 250° C. The reaction conditions are preferably mildly to very mildly acidic. Preferably [H$^+$]≤about 500 mM, more preferably [H$^+$]≤about 100 mM, more preferably still [H$^+$]≤about 50 mM. Preferred acidities are from about 5 mM [H$^+$] to about 50 mM [H$^+$]. The acidity can be provided

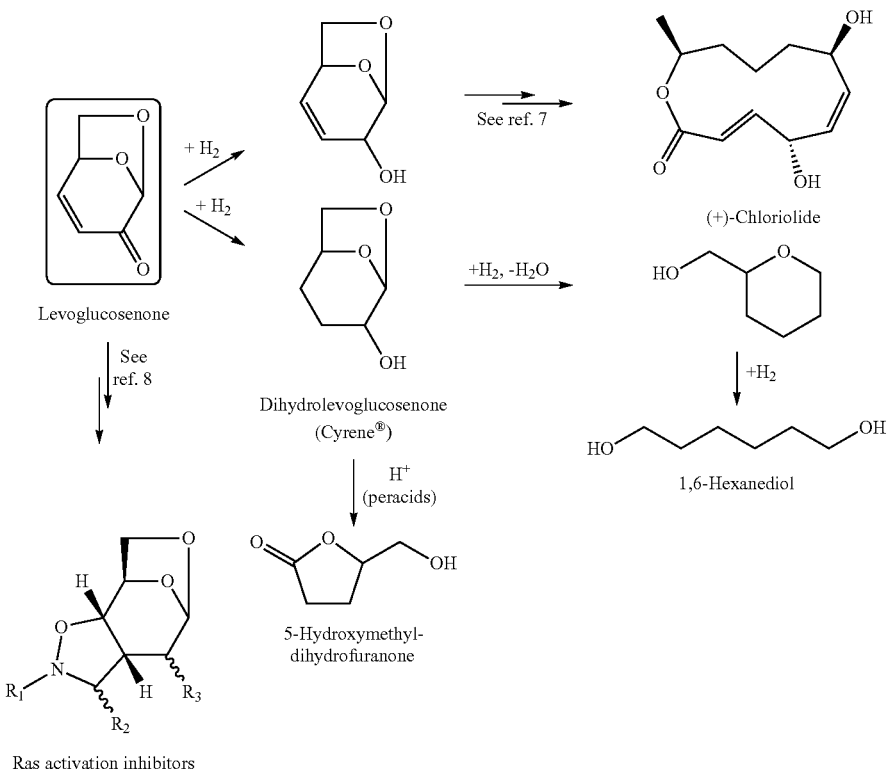

Scheme 1. Chemicals that can be produced from LGO

LGO has traditionally been produced by catalytic fast pyrolysis of biomass, and many attempts have been made to improve the LGO yield using pyrolysis technologies. Notably, Dobele and coworkers pre-treated wood with phosphoric acid prior to pyrolysis, with LGO making up 30% of the by any suitable acid, such as mineral acid (e.g., HCl, HNO$_3$, H$_2$SO$_4$, and the like.) In this system, levoglucosan is the major decomposition product of cellulose found in the biomass. The levoglucosan is then dehydrated to yield LGO. The entire process is shown in Scheme 2:

Scheme 2. Cellulose to LGO

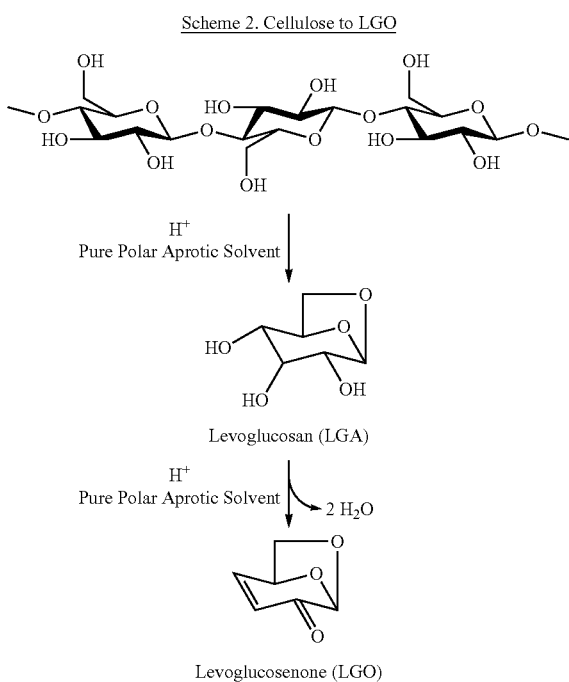

Glucose, levulinic acid and formic acid are also produced as a result of side reactions with water, which is formed as a by-product of the levoglucosan dehydration reaction. The turnover frequency for cellulose conversion increases as the water content in the solvent decreases, with conversion rates in THF being more than twenty times higher than those in water. Thus, it is preferred that the initial reaction solvent be substantially water-free. As shown in the Examples, the highest LGO yields from cellulose were achieved using tetrahydrofuran (THF; 12 wt % yield) and gamma valerolactone (GVL; 22 wt % yield) as the solvents, which are comparable to or better than the yields obtained in ionic liquids. Moreover, the use of a low boiling point, aprotic polar solvent, such as THF, facilitates recovery of the LGO in downstream processes.

Thus, disclosed herein is a method to produce levoglucosenone (LGO) from cellulosic biomass, including cellulose, lignocellulose, cellobiose, and/or glucose. The method comprises reacting a reactant comprising cellulose, lignocellulose, cellobiose, or glucose or a combination thereof, in a reaction mixture comprising a polar, aprotic solvent and an acid, for a time, at a temperature, and at a hydrogen ion concentration wherein at least a portion of the cellulose, lignocellulose, cellobiose, or glucose present in the reactant is converted to HMF. Optionally, the reaction mixture is initially substantially devoid of water.

Preferably, the acid is present in an amount to yield a hydrogen ion concentration in the reaction mixture of from about 5 mM to about 500 mM, or from about 5 mM to about 100 mM, or from about 5 mM to about 50 mM. The acid may be a Brønsted-Lowry acid, although this is not required. The acid may be a Lewis acid. Mineral acids are most preferred.

The reaction may be carried out at any suitable temperature. However, it is preferred that the reaction temperature is from about 80° C. to about 500° C., more preferably from about 80° C. to about 400° C., more preferably still from about 80° C. to about 300° C., and most preferably from about 140° C. to about 250° C. Any polar, aprotic solvent may be used in the method. Such solvents include, for example (and not by way of limitation), beta-, gamma-, and delta-lactones, hydrofurans, hydropyrans, and combinations thereof, such as gamma valerolactone. The polar, aprotic solvent may be selected from the group consisting of dihydrolevoglucosenone, 6,8-dioxabicyclo-octane, dichloromethane, tetrahydrofuran, ethylacetate, acetone, dimethylformamide, acetonitrile, dimethylsulfoxide, propylene carbonate, N-methyl-2-pyrrolidone, and hexamethylphosphoramide.

In a second version of the method, the reaction mixture comprises no more than about 2.0 wt % water at any time during the reaction. All of the other considerations noted above for acid type, hydrogen ion concentration, solvent type, etc. apply to this version of the method as well. Thus, the method explicitly includes reacting a reactant comprising cellulose, lignocellulose, cellobiose, or glucose, or a combination thereof, in a reaction mixture comprising a polar, aprotic solvent and an acid, for a time, at a temperature, and at a hydrogen ion concentration wherein at least a portion of the cellulose, lignocellulose, cellobiose, or glucose present in the reactant is converted to LGO. Again, and optionally, the reaction mixture may be initially substantially devoid of water; and wherein the reaction mixture comprises no more than about 2.0 wt % water at any time during the reaction.

In the second version of the method, the acid is preferably present in an amount to yield a hydrogen ion concentration in the reaction mixture of from about 5 mM to about 500 mM, or from about 5 mM to about 100 mM, or from about 5 mM to about 50 mM. The acid may be a Brønsted-Lowry acid, although this is not required. The acid may be a Lewis acid. Mineral acids are most preferred.

In the second version of the method, the reaction may be carried out at any suitable temperature. However, it is preferred that the reaction temperature is from about 80° C. to about 500° C., or from about 80° C. to about 400° C., or from about 80° C. to about 300° C., or from about 140° C. to about 250° C.

Any polar, aprotic solvent may be used in the second version of the method. Such solvents include, for example (and not by way of limitation), beta-, gamma-, and delta-lactones, hydrofurans, hydropyrans, dihydrolevoglucosenone, 6,8-dioxabicyclo-octane, and combinations thereof, such as gamma valerolactone. The polar, aprotic solvent may be selected from the group consisting of dichloromethane, tetrahydrofuran, ethylacetate, acetone, dimethylformamide, acetonitrile, dimethylsulfoxide, propylene carbonate, N-methyl-2-pyrrolidone, and hexamethylphosphoramide.

The method disclosed herein offers several advantages over conventional approaches to making LGO, including low reaction temperature, high yield, and simple product distribution. The desired LGO product is easily separated from the reaction solvent and by-products.

BRIEF DESCRIPTION OF THE DRAWINGS

FIG. 2A: GVL, 170° C., 5 mM $H_2SO_4$. FIG. 2B: THF, 170° C., 5 mM $H_2SO_4$. FIG. 2C: GVL 190° C., 7.5 mM $H_2SO_4$. FIG. 2D: THF, 190° C., 7.5 mM $H_2SO_4$. LGO (■); LGA (●); HMF (▲); glucose (▼); furfural (◄).

FIG. 5A: LGO yield. FIG. 5B: HMF yield. FIG. 5C: LGA yield. FIG. 5D: Glucose yield. Pure THF (■); 2.7% water in THF (●); 11.6% water in THF (▲). Increasing the water content of the solvent inhibits LGO formation.

DETAILED DESCRIPTION

Abbreviations and Definitions

Figure 1:
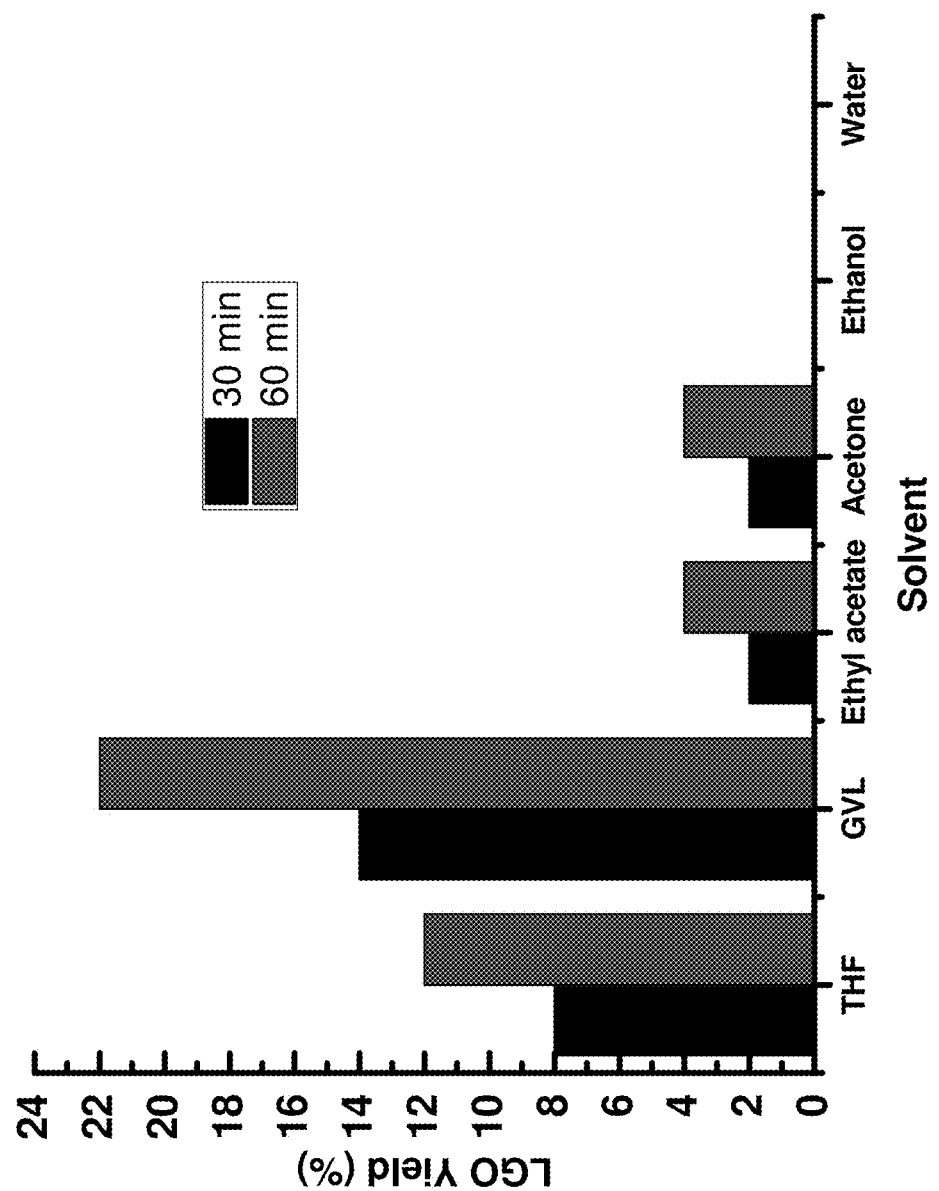
FIG. 1 is a histogram depicting effect of solvent on LGO yield. The highest yields were in GVL and THF; the lowest yields were in ethyl acetate and acetone. Reaction Conditions: 170° C., 1000 psig He, 5 wt % cellulose feed, 5 mM $H_2SO_4$, 60 mL total volume.

DMA=N,N-dimethylacetamide. DMF=2,5-dimethylfuran. FA=formic acid. FDCA=2,5-furandicarboxylic acid. Fur=furfural. GVL=gamma-valerolactone. HMF=5-hydroxymethyl furfural. LA=levulinic acid. LGA=levoglucosan. LGO=levoglucosenone. THF=tetrahydrofuran. TOF=turnover frequency.

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass. Glucose for use in the disclosed method may be biomass-derived.

"Brønsted-Lowry Acid/Base"=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers ($(C_6H_{10}O_5)_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose.

"Glucose-containing oligomers, glucose-containing polymers, Glucose-containing reactant, C6-containing reactant"=Any chemical species, having any type of intramolecular bond type, that comprises a glucose unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose are explicitly included within the definition.

"Homogeneous catalyst"=A catalyst that exists in the same phase (solid, liquid, or gas) as the reactants under reaction conditions. "Heterogeneous catalyst"=A catalyst that exists in a different phase than the reactants under reaction conditions.

"Hydrofuran" is used herein to refer to any unsubstituted or substituted cyclic ether having a single oxygen heteroatom in the ring, and having five total atoms in the ring and which is derived from furanic compounds. Hydrofurans that are miscible in water, such as tetrahydrofuran (THF), are more appropriate for use in the monophasic reactions described herein.

"Hydropyran" is used herein to refer to any unsubstituted or substituted cyclic ether having a single oxygen heteroatom in the ring, and having six total atoms in the ring and which is derived from pyranic compounds. Hydropyrans miscible in water are more appropriate for use in the monophasic reactions described herein.

"Lactone" as used herein refers to an unsubstituted or substituted cyclic ester, having a single oxygen heteroatom in the ring, and having from four to six total atoms in the ring—i.e., beta, gamma, and delta lactones, derived from any corresponding C4 to C16 carboxylic acid. Thus, as used herein, the term "lactone" explicitly includes (without limitation) unsubstituted and substituted beta and gamma-butyrolactone and beta-, gamma-, and delta-valerolactones to beta-, gamma, and delta-hexadecalactones. Some lactones are miscible in water, such as GVL; other lactones have more limited solubility in water.

"Lewis Acid/Base"=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, (alkyl)$AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$. and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, silica-alumina, acid clays, sulfated zirconia, phosphates such as zirconium phosphate, molecular sieve materials, zeolites, and acidic material on a thermally stable support. Where an acidic material is provided on a thermally stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Total Carbon Yield:

$$\text{Tot. C Yield (\%)} = 100 \times \frac{\text{total moles of carbon from all detectable products*}}{\text{initial moles of carbon in feed}}$$

Relative Carbon Selectivity (%):

$$[\text{Relative carbon selectivity}]_i (\%) = 100 \times \frac{\text{moles of carbon of product i}}{\text{total moles of carbon from all detectable products}}$$

Carbon Yield:

$$[\text{Carbon yield}]_i (\%) = 100 \times \frac{\text{moles of carbon of product i}}{\text{initial moles of carbon in feed}}$$

Turnover Frequency:

$$\text{Turnover frequency}(hr^{-1}) = \frac{d(\text{total moles of carbon produced})}{dt} \times \frac{1}{\text{moles of protons}}$$

*Detectable products: glucose, LGA, LGO, FA, LA, HMF, Fur.

"Mineral acid"=an acid derived from one or more inorganic compounds. Examples include, but are not limited to hydrochloric acid (HCl), nitric acid ($HNO_3$), phosphoric acid ($H_3PO_4$), sulfuric acid ($H_2SO_4$) boric acid ($H_3BO_3$), hydrofluoric acid (HF), hydrobromic acid (HBr), perchloric acid ($HClO_4$), and the like.

"Polar, aprotic solvent"=Any solvent having a net positive dipole moment, a relatively high dielectric constant, and which lacks a labile (acidic) hydrogen atom. Examples of polar, aprotic solvents include, but are not limited to, dichloromethane, hydrofurans (e.g. tetrahydrofuran), hydropyrans, ethylacetate, acetone, dimethylformamide, acetonitrile, dimethylsulfoxide, propylene carbonate, N-methyl-2-pyrrolidone, hexamethylphosphoramide, and the like.

"Substantially devoid of" means that the listed item, ingredient, or reagent is initially present in an amount of from 0 wt % to no more than 0.5 wt % of the total composition.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

Overview

Disclosed herein is a method to produce LGO and LGA from cellulose-containing biomass in polar aprotic solvents in the substantial absence of water as a co-solvent. The method is able to produce LGO from cellulosic biomass in yields that approach those obtained in ionic liquids or biphasic systems. Moreover, LGO and other reaction byproducts can be separated from the polar aprotic solvent using conventional separation technologies like distillation and evaporation (by way of example and not limitation).

Disclosed herein is a method to produce LGO from cellulose under mild reaction conditions using polar, aprotic solvents such as THF and GVL. The yield of LGO is higher than can be obtained using ionic liquids or sulfolane. Moreover, HMF and furfural are the only volatile by-products, and these can be easily removed by distillation. Additionally, the product distribution can be adjusted by optimizing the reaction conditions.

Product Quantification and Identification:

The main detectable products from the reaction are glucose, LGA, LGO, furfural, HMF, levulinic acid, and formic acid. Gas chromatography (GC) is typically used to analyze many of these compounds when studying catalytic fast pyrolysis. Glucose and LGA, however, must be analyzed using liquid phase techniques such as liquid chromatography (HPLC). The Biorad Aminex HPX-87H organic acid column (BioRad, Inc., Hercules, Calif.) that is typically used in HPLC analyses cannot resolve LGO from HMF. This lack of resolution is not typically a problem in systems where hydrolysis is the target reaction because little LGO is formed except under anhydrous conditions (discussed below). In contrast, analysis by GC resolves LGO from HMF, but glucose, LGA, and formic acid are not detected due to decomposition of glucose and LGA in the injector and poor sensitivity of formic acid. Therefore, reactions performed in the liquid phase need to be analyzed by both GC and HPLC in order to adequately quantify all of the potential products.

Solvent Selection:

As discussed above, the presence of LGO can convolute the results obtained by the standard analytical method using only HPLC. Thus, the dehydration of cellulose into LGO was explored in different solvents. The results are depicted in FIG. 1, which is a histogram depicting effect of solvent on LGO yield. The highest yields were in GVL and THF; the lowest yields were in ethyl acetate and acetone. The protic solvents water and ethanol gave essentially no LGO yield. The reaction conditions for all solvents tested were 170° C., 1000 psig He, 5 wt % cellulose feed, 5 mM $H_2SO_4$, in 60 mL total volume.

The use of water and ethanol, both of which are protic solvents, resulted in the lowest yields of LGO. The use of acetone and ethyl acetate led to 2-3% yields of LGO, while the use of THF and GVL led to the highest yields of LGO, with increasing yields obtained at longer reaction times. (The results of 30 min and 60 min run times are depicted in FIG. 1).

Figures 2A, 2B:
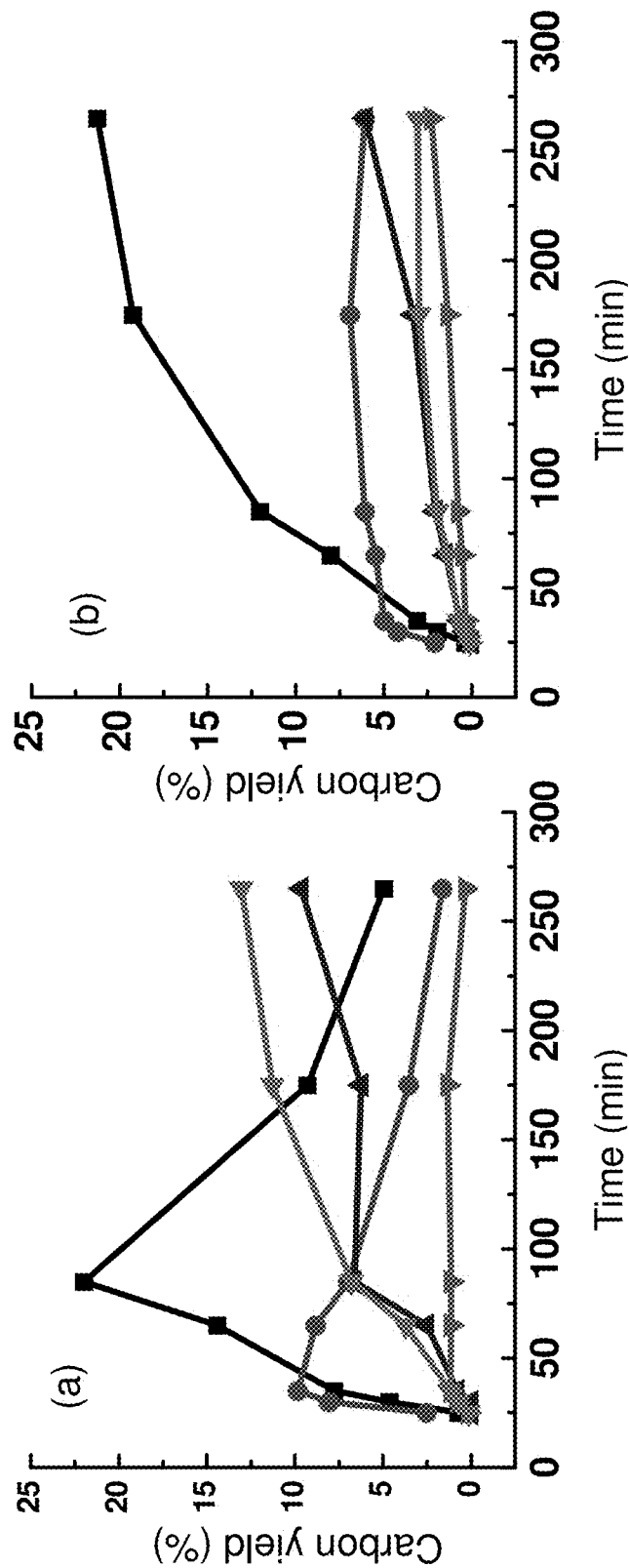
FIGS. 2A, 2B, 2C, and 2D are a series of graphs depicting the influence of solvent and reaction time on product yields. All reactions were carried out at 1000 psig He, 5 wt % cellulose feed, in 60 mL total volume.
Figures 2C, 2D:
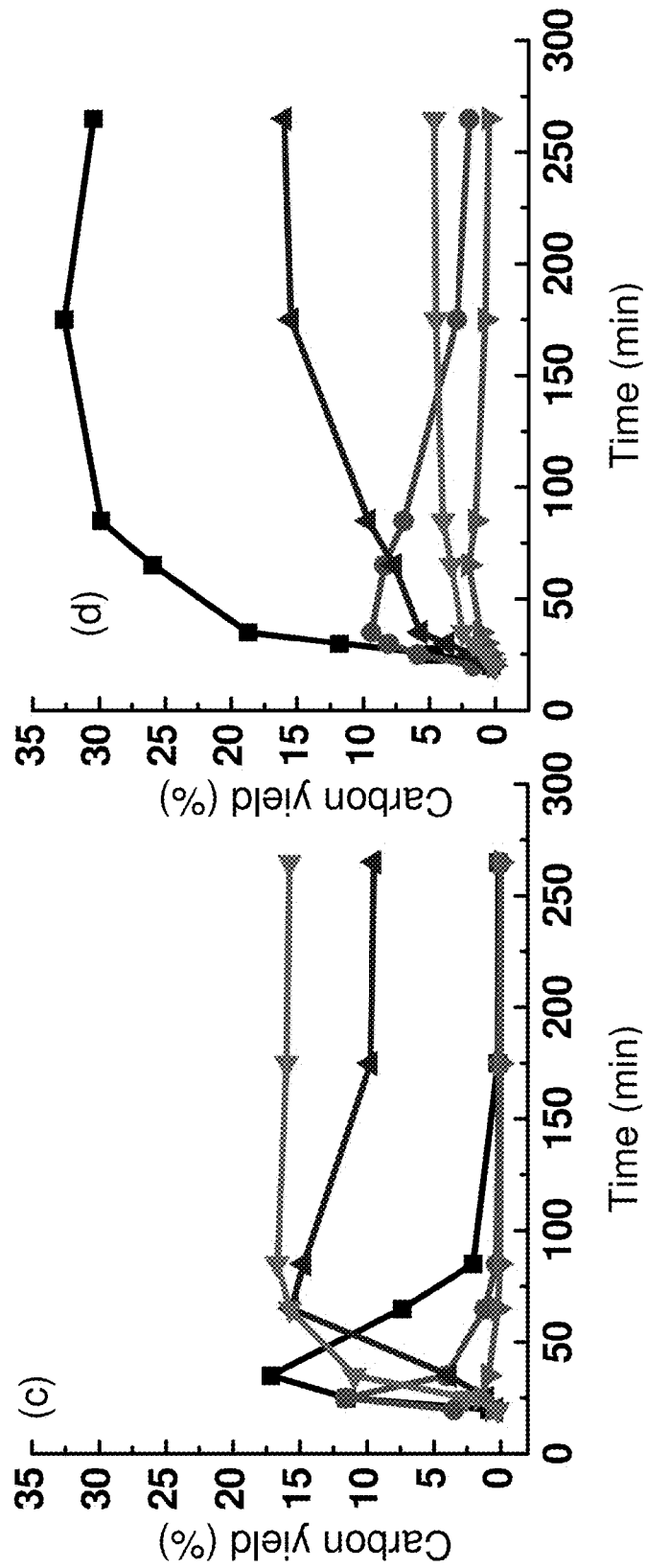

Consequently, the yield of LGO as a function of reaction time using both GVL and THF as solvents at both 170° C. and 190° C. was explored. See FIGS. 2A, 2B, 2C, and 2D. FIG. 2A: GVL, 170° C., 5 mM $H_2SO_4$. FIG. 2B: THF, 170° C., 5 mM $H_2SO_4$. FIG. 2C: GVL 190° C., 7.5 mM $H_2SO_4$. FIG. 2D: THF, 190° C., 7.5 mM $H_2SO_4$. LGO (■); LGA (●); HMF (▲); glucose (▼); furfural (◄). Though higher yields of LGO from cellulose are initially obtained in GVL, the yield of LGO in THF increased continuously, eventually matching the maximum yield obtained in GVL.

Importantly, LGO appears to be stable in THF at long reaction times whereas LGO degrades in GVL. See FIG. 3, which depicts the results of a study of LGO stability in THF. At 190° C., higher yields of LGO were obtained when using THF than when using GVL. Though the initial rates of LGO and LGA in GVL were higher than in THF at 170° C., the opposite results was observed at 190° C. The rate of HMF production relative to the rate of LGO production in GVL is twice that in THF, suggesting that GVL promotes the formation of HMF. See also Table 2.

TABLE 2

Initial rate of LGO, LGA and HMF in different solvents at 170° C. or 190° C. Reaction condition: Cellulose loading 5 wt %, Solvent volume 60 mL. [a] The LGA production rate is sufficiently high at this condition that the maximum LGA concentration was achieved prior to taking the first sample.

| Solvents | Temp. [° C.] | Acid [mM] | Initial rate [mmol $L^{-1}$ $min^{-1}$] | | | HMF:LGO |
|---|---|---|---|---|---|---|
| | | | LGO | LGA | HMF | |
| THF | 170 | 5 | 0.29 ± 0.03 | 0.07 ± 0.03 | 0.05 ± 0.01 | 0.17 |
| THF | 190 | 7.5 | 1.01 ± 0.27 | 0.55 ± 0.08 | 0.18 ± 0.04 | 0.18 |
| GVL | 170 | 5 | 0.51 ± 0.05 | 1.11 ± 0.33 | 0.18 ± 0.01 | 0.35 |
| GVL | 190 | 7.5 | 0.87 ± 0.06 | n.d.[a] | 0.37 ± 0.16 | 0.43 |

Dihydrolevoglucosenone (Cyrene-brand solvent) and 6,8-dioxabicyclo-octane are also suitable solvents, especially for the production of 1,6-hexanedione. The solubility of LGO is significantly higher in these two solvents than is the solubility of the LGO hydrogenation products. This greatly eases separating the desired 1,6-hexanediol product from the solvent and unreacted LGO:

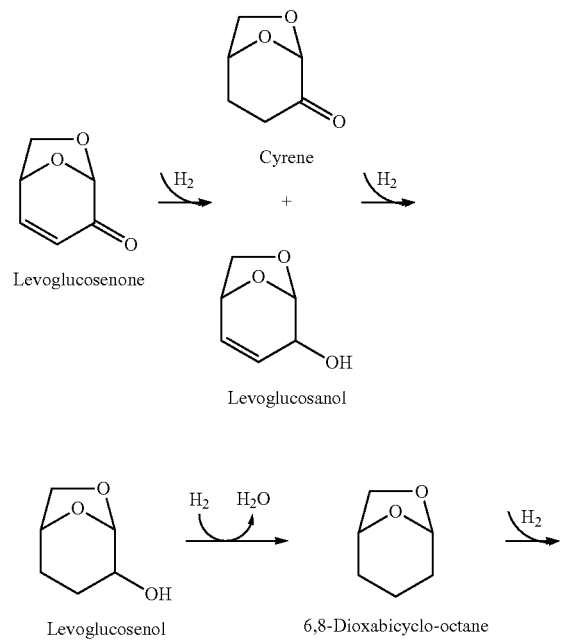

-continued

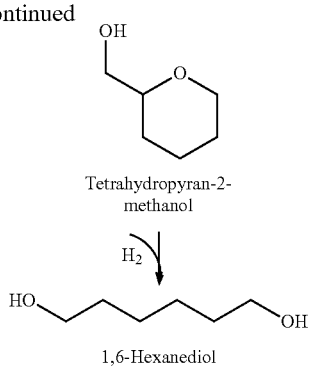

Tetrahydropyran-2-methanol

↓ H₂

1,6-Hexanediol

Figure 4:
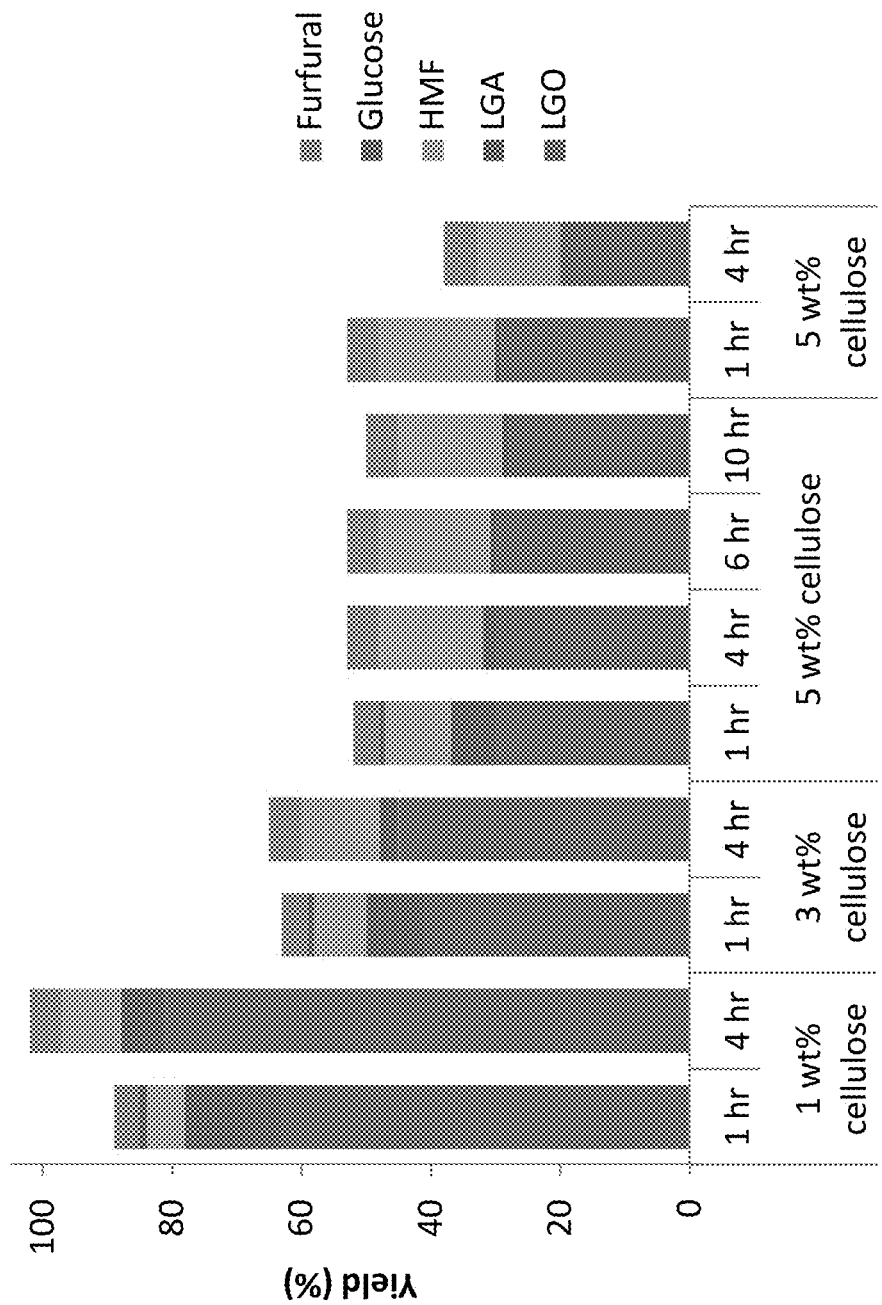
FIG. 4 is a histogram depicting the effect of cellulose loading and acid concentration on product yields. Reaction conditions: 190° C., pure THF, 1000 psig He, 60 mL total volume. LGO concentrations at high cellulose loadings was approx. 13 g/L at all reaction conditions.

Effect of Cellulose Loading and Acid Concentration:

Next was examined the effect on the product yield of cellulose loadings ranging from 1 to 5 wt % and $H_2SO_4$ loadings of 7.5 or 20 mM. See FIG. 4 and Table 3. As shown in Table 3, the yield of LGO decreases from 81% to 30% with increasing cellulose loading. Interestingly, the LGO concentration remained invariant regardless of cellulose loading (see FIG. 4), while the highest LGO yield was obtained from 1 wt % cellulose. Meanwhile, the total carbon yield and the yield of LGA also decreased with increasing cellulose loading. The yield of glucose was always low due to the absence of water in these reactions. In contrast, the yield and concentration of HMF increased with increasing cellulose loadings while the yield of furfural remained constant. At longer reaction times, the yields of all compounds except furfural decreased. Increasing the acid catalyst amount had a minimal effect on the LGO yield.

TABLE 3

Effect of cellulose loading and sulfuric acid concentration on reaction products. Reaction condition: THF (60 mL), T = 190° C.

| Cellulose [%] | Sulfuric acid [mM] | Time[a] [h] | Yield [%] | | | | | |
|---|---|---|---|---|---|---|---|---|
| | | | LGO | LGA | HMF | Glucose | Furfural | Total |
| 1 | 7.5 | 1 | 63 | 15 | 6 | 1 | 4 | 88 |
| | | 4 | 81 | 7 | 9 | 0 | 5 | 103 |
| 3 | 7.5 | 1 | 41 | 9 | 8 | 1 | 4 | 63 |
| | | 4 | 45 | 3 | 12 | 0 | 5 | 66 |
| 5 | 7.5 | 1 | 30 | 7 | 10 | 1 | 4 | 52 |
| | | 4 | 30 | 2 | 16 | 0 | 5 | 54 |
| | | 6 | 30 | 1 | 17 | 0 | 5 | 53 |
| | | 10 | 28 | 1 | 16 | 0 | 5 | 50 |
| 5 | 20 | 1 | 29 | 1 | 18 | 0 | 5 | 53 |
| | | 4 | 20 | 0 | 13 | 0 | 5 | 38 |

[a]Starting from reaching reaction temperature.

Figures 5A, 5B:
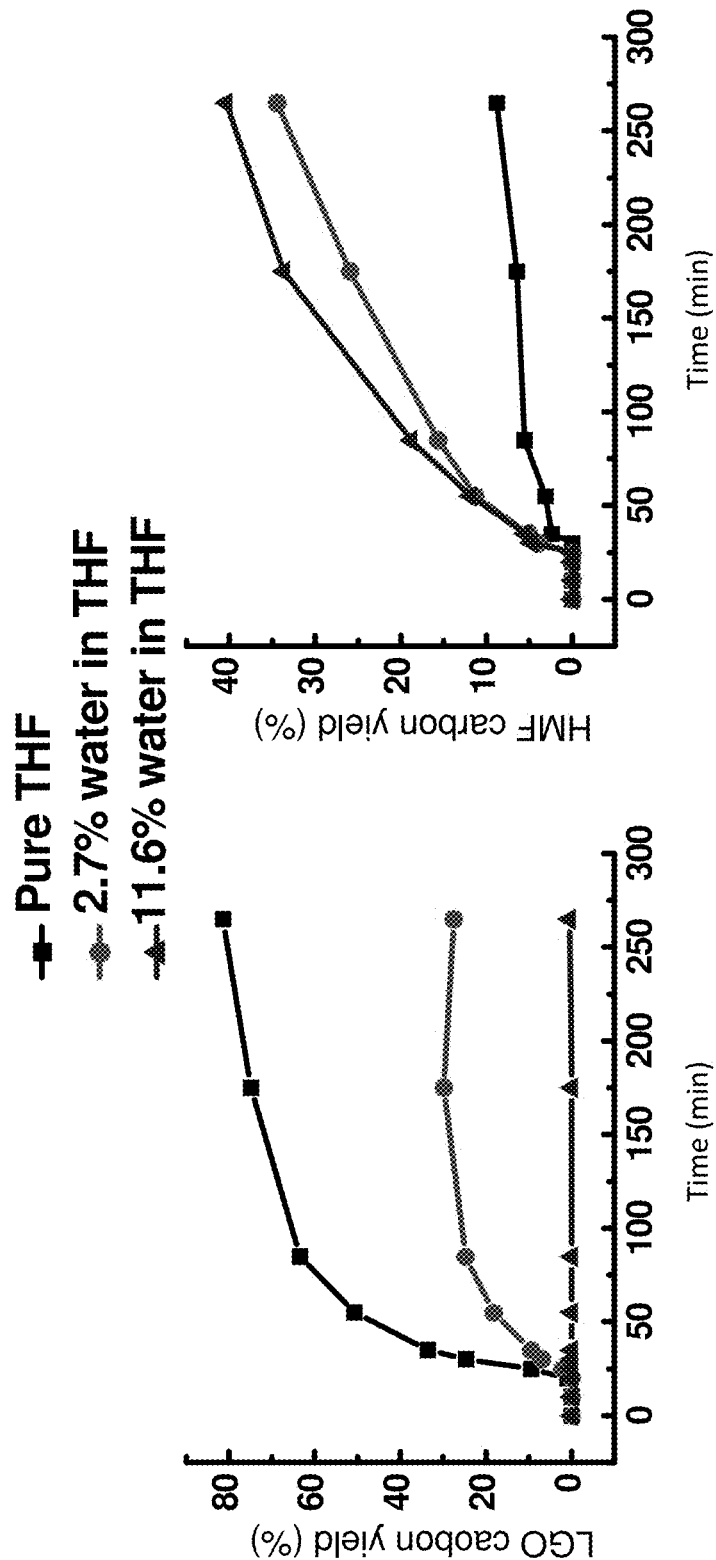
FIGS. 5A, 5B, 5C, and 5D are a series of graphs depicting the influence of water content on product yields. All reactions were carried out at 190° C., pure THF, 1 wt % cellulose, 1000 psig He, and 60 mL total volume.
Figure 5C:
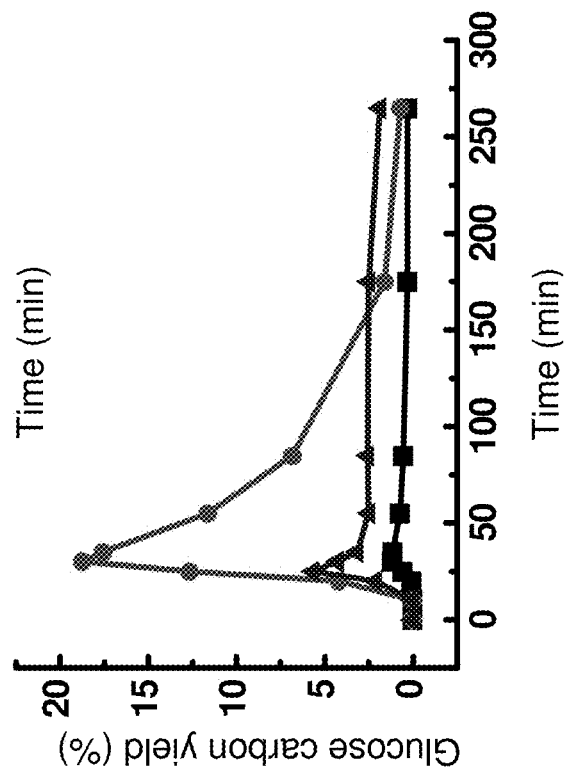
Figure 5D:
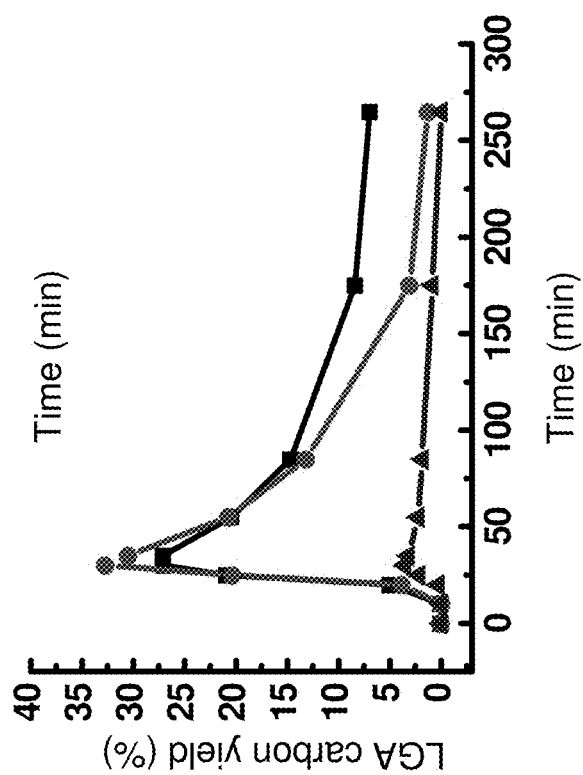

Effect of Water Content:

FIGS. 5A, 5B, 5C, and 5D show the effect of water content on the dehydration of cellulose in THF at 190° C. (FIG. 5A: LGO yield. FIG. 5B: HMF yield. FIG. 5C: LGA yield. FIG. 5D: Glucose yield.) In pure THF, cellulose rapidly depolymerizes to LGA, and the LGA is gradually converted to LGO. The maximum yield of LGO was 81%, achieved after 4 hours of reaction. Only a trace amount of glucose was detected when using pure solvents, and the water required for hydrolysis likely comes from the dehydration of LGA.

As shown in FIGS. 5A, 5B, 5C, and 5D, the conversion of cellulose to glucose was dramatically enhanced by the addition of 2.7 wt % water. LGA and glucose, obtained from cellulose dehydration and hydrolysis, respectively, were both detected at short reaction times (30 minutes). The highest yields of LGA and glucose were 33 and 19%, respectively. Notably, the yield of LGO with 2.7% water decreased by half compared to that obtained in pure THF. The HMF yield increased two-fold with the addition of 2.7 wt % water to the THF. Cellulose dehydration to LGO was completely inhibited in the presence of 11 wt % water, while cellulose hydrolysis to glucose was promoted. The glucose went through a maximum with time on stream, suggesting that it is rapidly converted to HMF and humins. The formation of humins was indicated by insoluble precipitates in the reactor. Interestingly, the yield of furfural remained essentially constant in regardless of the presence of water and despite the increase in the HMF yield with increasing water content.

Figure 6:
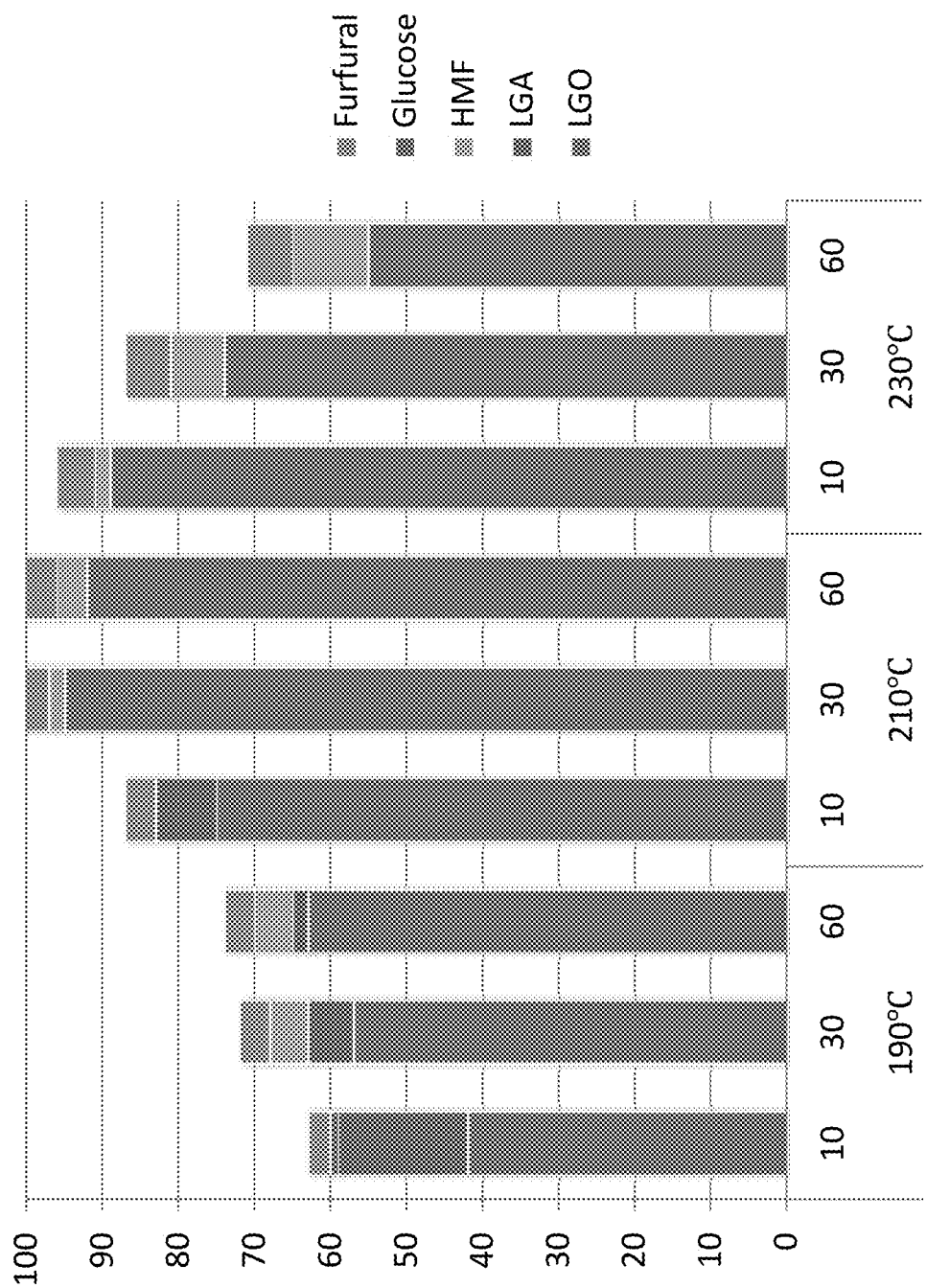
FIG. 6 is a histogram depicting the effect of temperature on product yields. Reaction conditions: Pure THF, 1000 psig He, 1 wt % cellulose, 20 mM $H_2SO_4$, 60 mL total volume. As shown in the figure, the optimum temperature under these conditions was about 210° C. applied for 30 min.

Effect of Temperature:

Increasing the reaction temperature promoted the production of LGO as shown in FIG. 6 and Table 4. A maximum LGO yield of 95% was obtained after 30 min at 210° C. Further increasing the temperature shortened the optimum time to less than 10 min. A similar improvement in yield was observed at a 3% cellulose loading. The reaction solution contained only LGO, HMF, and furfural when the reaction was stopped.

TABLE 4

Effect of temperature on LGO production. Reaction condition: THF (60 mL), Sulfuric acid concentration 20 mM.

| Cellulose [%] | T [° C.] | Time[a] [min] | Yield [%] | | | | |
|---|---|---|---|---|---|---|---|
| | | | LGO | LGA | HMF | Gluc | Fur | Total |
| 1 | 190 | 10 | 42 | 17 | 0 | 1 | 3 | 63 |
| | | 30 | 57 | 6 | 5 | 0 | 4 | 71 |
| | | 60 | 63 | 2 | 5 | 0 | 4 | 74 |
| 1 | 210 | 10 | 75 | 8 | 0 | 0 | 4 | 88 |
| | | 30 | 95 | 0 | 2 | 0 | 5 | 102 |
| | | 60 | 92 | 0 | 4 | 0 | 6 | 102 |
| 1 | 230 | 10 | 89 | 0 | 2 | 0 | 5 | 97 |
| | | 30 | 74 | 0 | 7 | 0 | 6 | 88 |
| | | 60 | 55 | 0 | 10 | 0 | 6 | 72 |
| 3 | 210 | 10 | 46 | 7 | 1 | 1 | 4 | 58 |
| | | 30 | 62 | 1 | 1 | 0 | 5 | 70 |
| | | 60 | 60 | 0 | 3 | 0 | 6 | 69 |

[a]Starting from reaching reaction temperature.

Interestingly, the maximum concentration of all LGO never exceeded 13 g L$^{-1}$ regardless of the reaction conditions (see FIG. 6). LGO is a relatively reactive compound at high temperature by comparison with the other reaction products.

Figure 3:
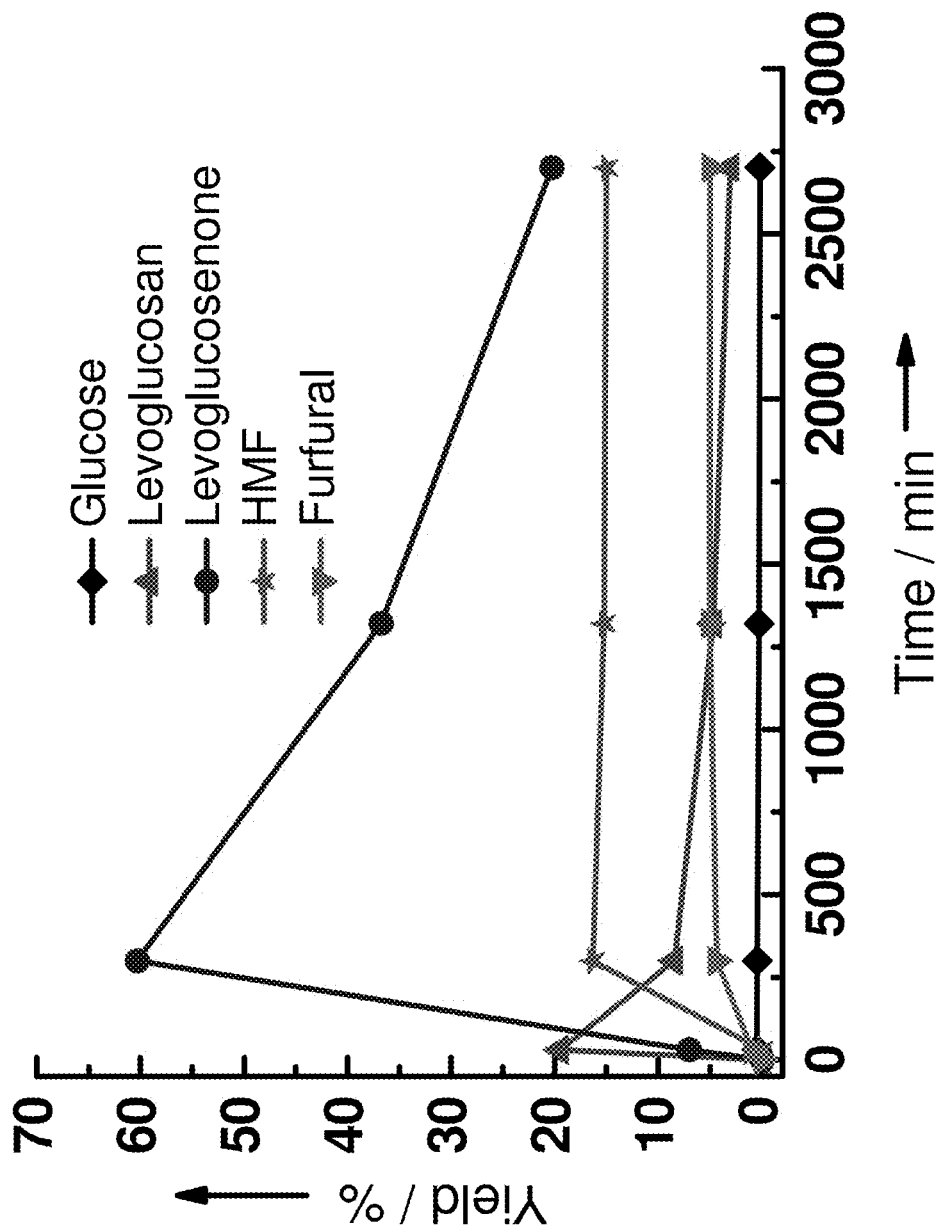
FIG. 3 is a graph depicting the stability of the LGO product over increasing reaction time. Reaction conditions: 190° C., pure THF, 1000 psig He, 1 wt % cellulose feed, 7.5 mM $H_2SO_4$, 60 mL total volume. Glucose (♦); LGA (▲); LGO (●); HMF (★); furfural (▼). As shown in the figure, in THF, LGO yield peaks prior to 500 minutes of reaction time and gradually decreases.

The Stability of LGO in THF:

While studying the effect of feedstock loading, we observed that the yield of LGO decreased after long reaction times (see FIG. 3). To confirm this result, a reaction was performed for 44.5 hr at 190° C. using 1 wt % cellulose in THF with 7.5 mM sulfuric acid as a catalyst. As shown in FIG. 3, the yield of LGO and the total yield reached a maximum at 4.5 h, after which the yields decreased gradually to one third of the maximum value. As noted above, LGA is a primary product which is consumed rapidly. No glucose was detected under anhydrous conditions. On the other hand, the HMF and furfural yields remained constant over the same time period.

Figure 7A:
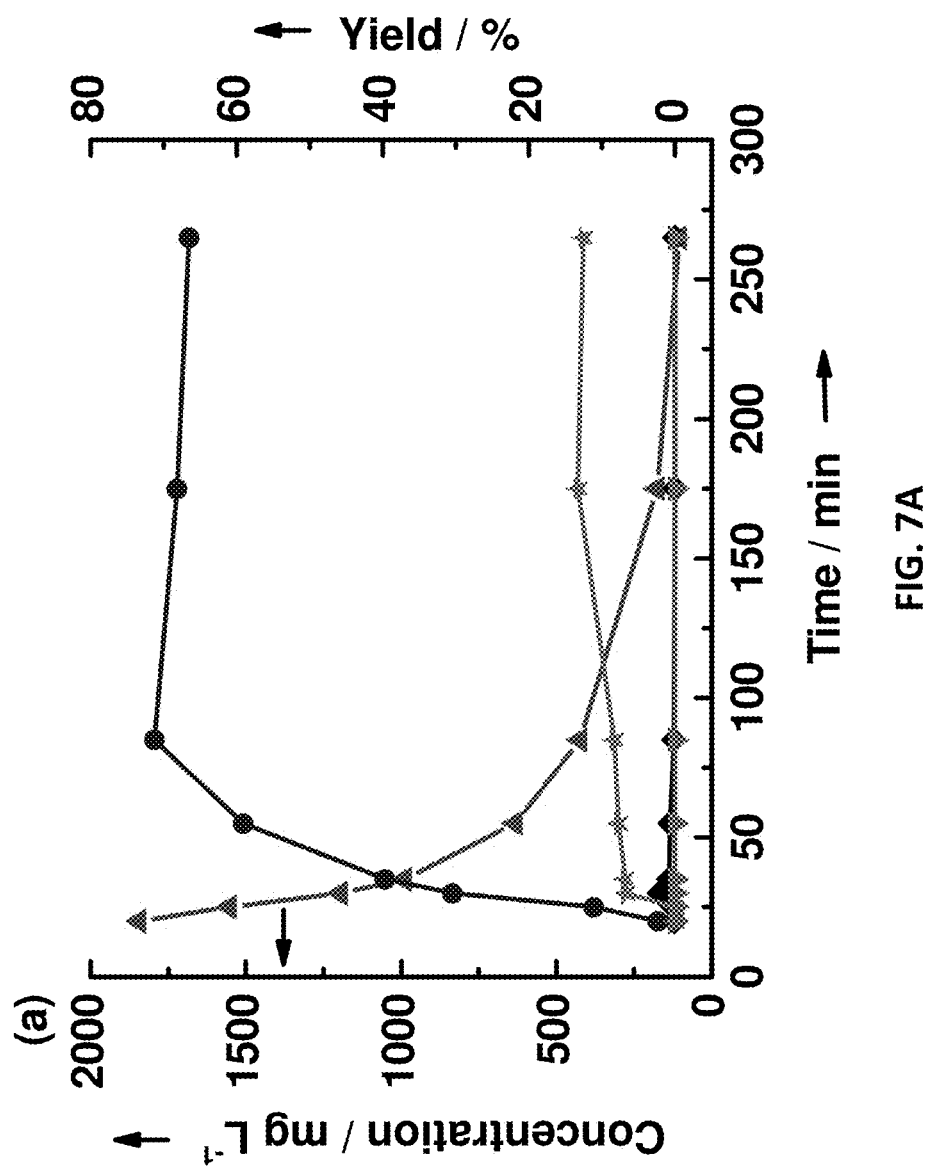
FIGS. 7A and 7B are graphs depicting the conversion of LGA to LGO in pure THF (FIG. 7A) and in 2.7% $H_2O$/THF (FIG. 7B). Reaction conditions: 190° C., 0.4 wt % LGA, 1000 psig He, 7.5 mM $H_2SO_4$, 60 mL total volume. LGA (●); glucose (■); LGO (▲), HMF (★); furfural (▼).
Figure 7B:
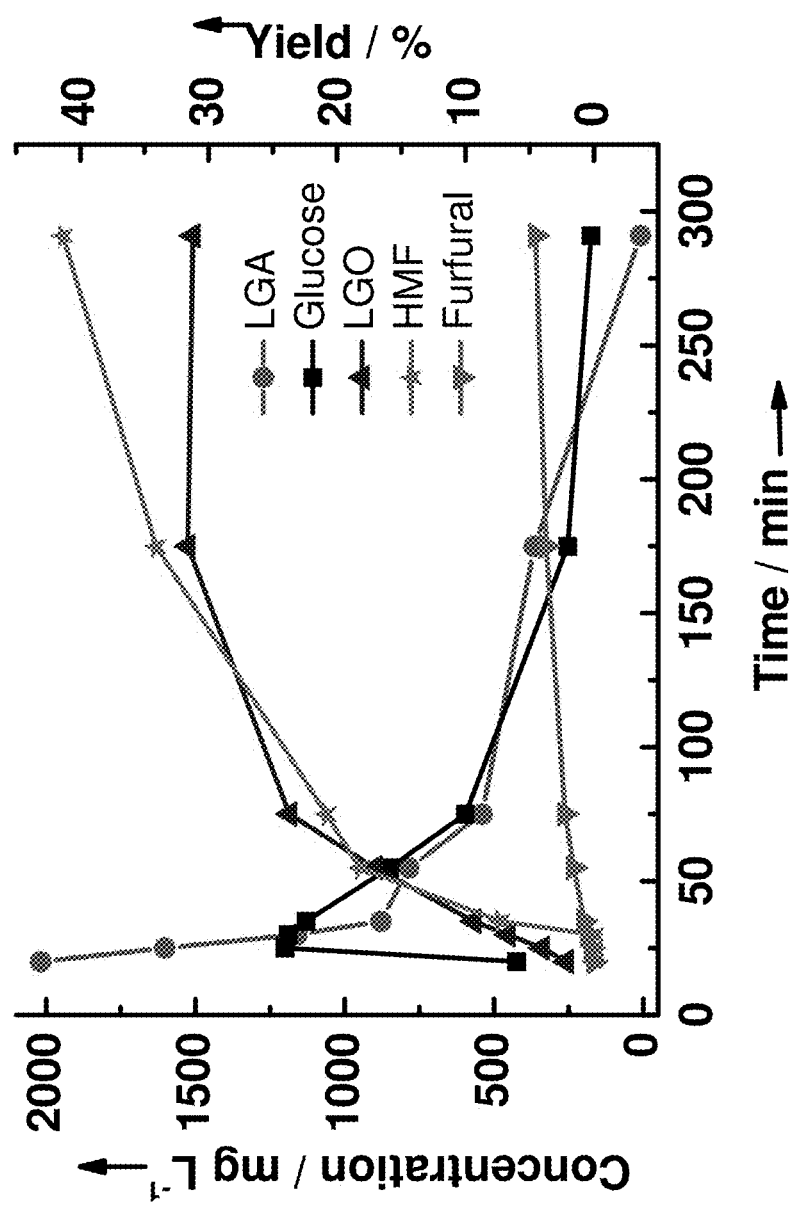
Figure 8A:
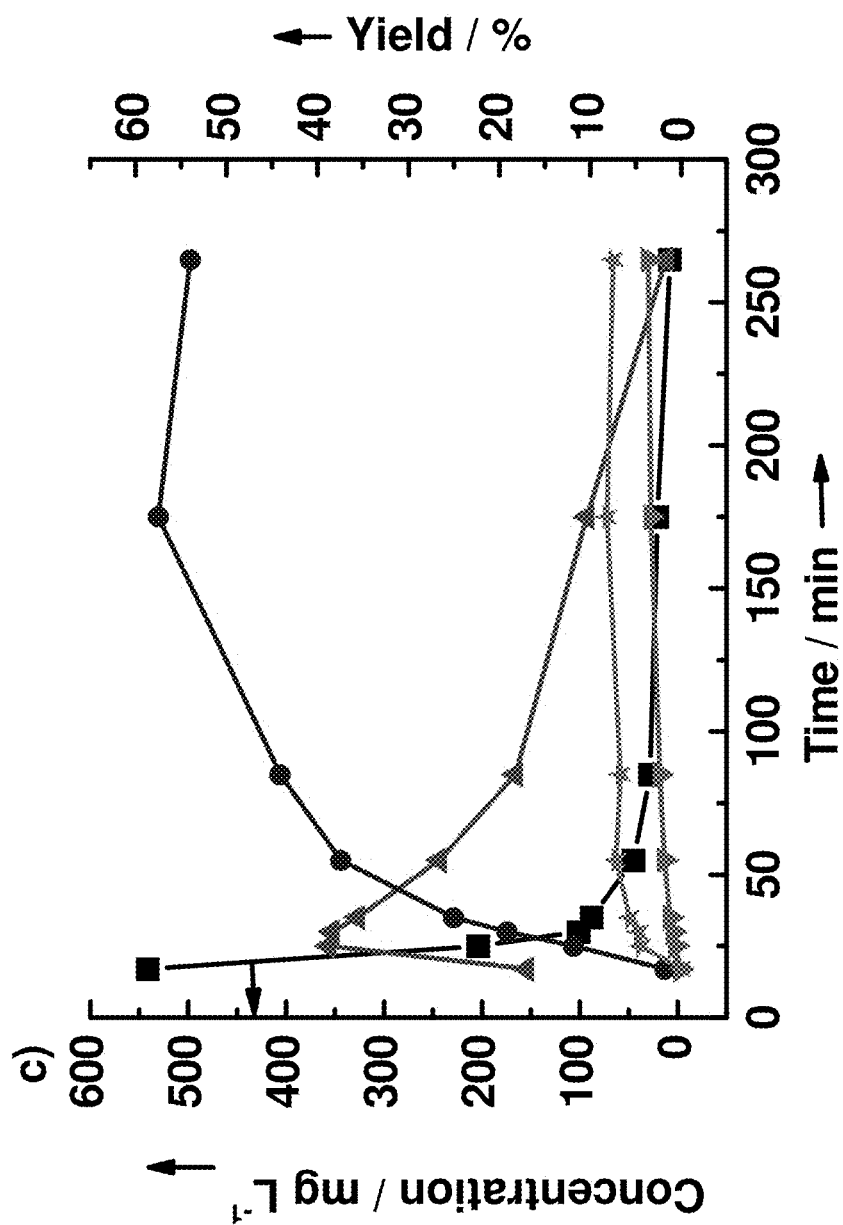
FIGS. 8A and 8B are graphs depicting the conversion of glucose to LGA to LGO in pure THF (FIG. 8A) and in 2.7% $H_2O$/THF (FIG. 8B). Reaction conditions: 190° C., 0.7 wt % glucose, 1000 psig He, 7.5 mM $H_2SO_4$, 60 mL total volume. Glucose (■); LGA (●); LGO (▲), HMF (★); furfural (▼).
Figure 8B:
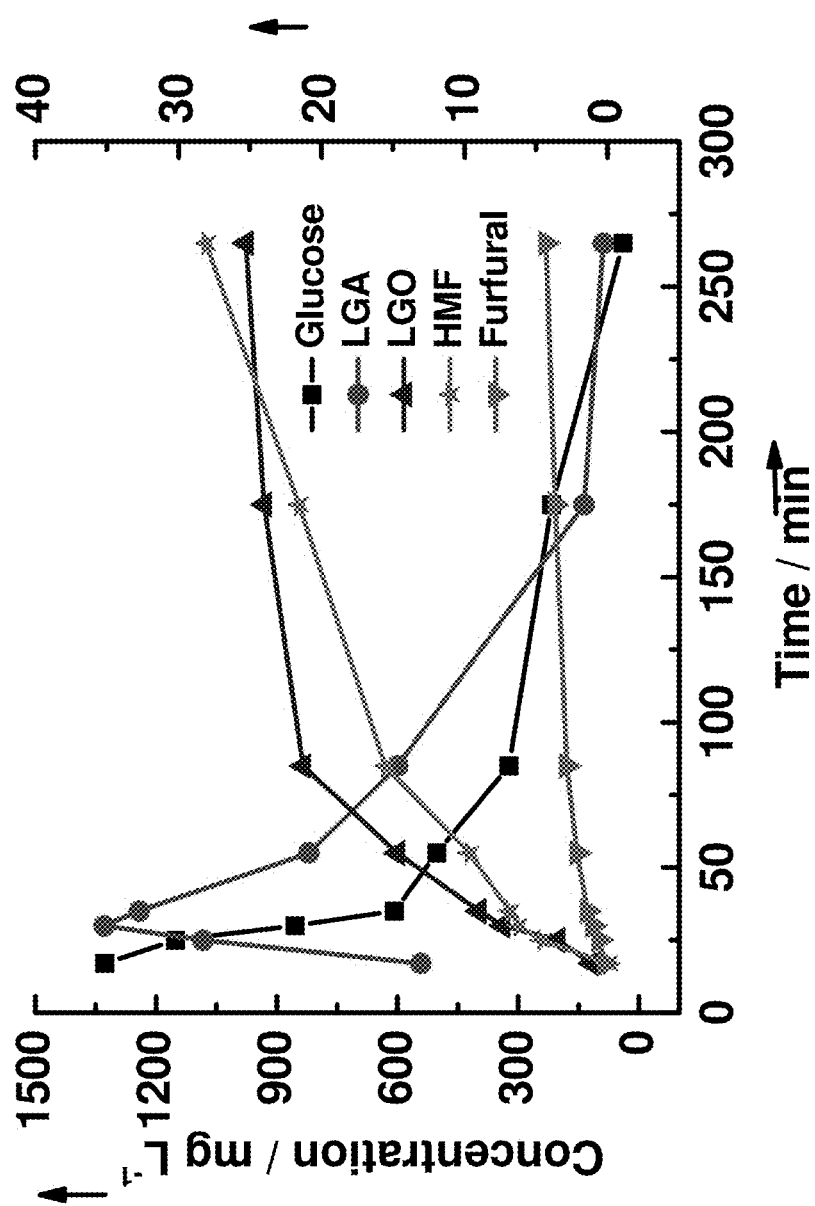
Figure 9:
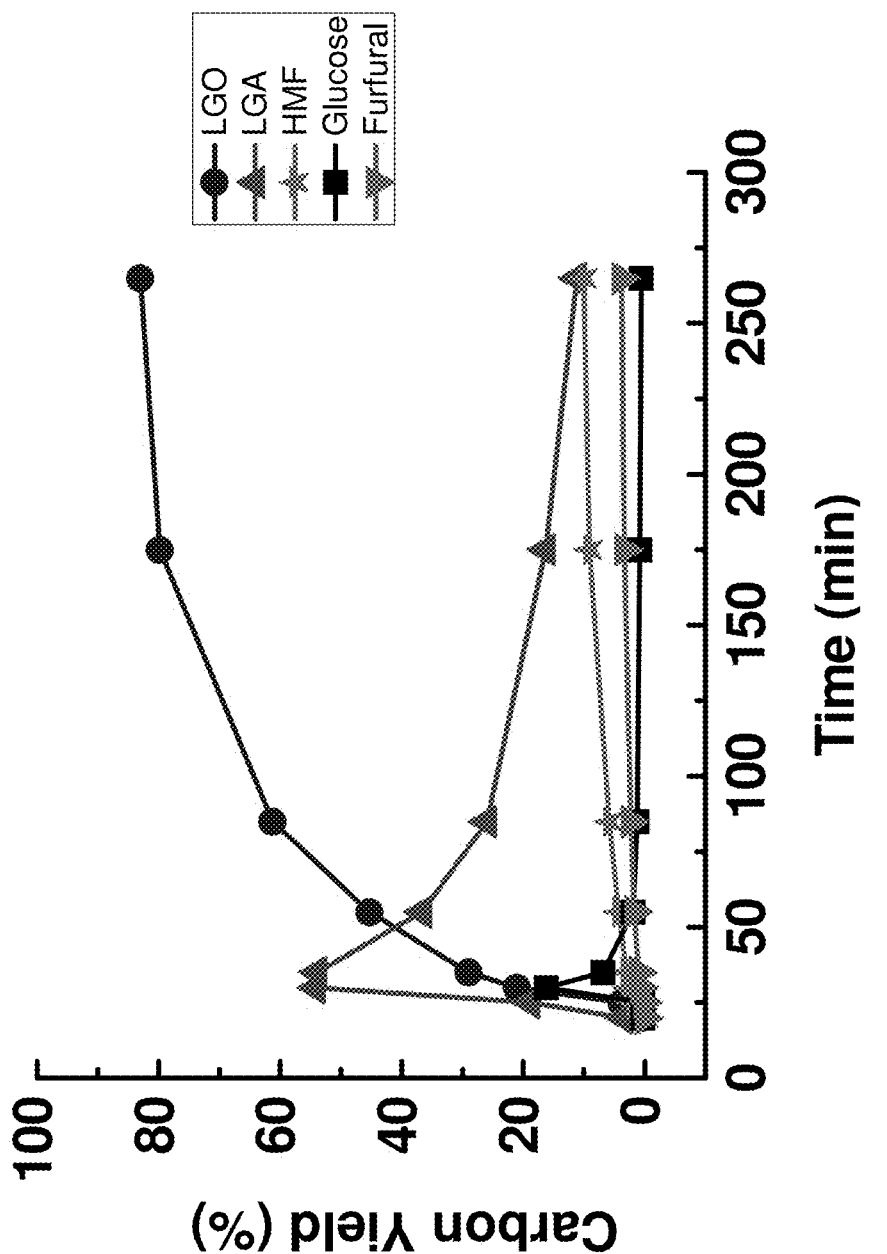
FIG. 9 is a graph depicting the conversion of cellobiose to LGA, LGO, and glucose. Reaction conditions: 190° C., 1.1 wt % cellobiose, 1000 psig He, 7.5 mM $H_2SO_4$, 60 mL total volume. LGO (●); LGA (▲), HMF (★); glucose (■); furfural (▼).

Elucidation of the Reaction Network:

FIGS. 7A and 7B show the results of the dehydration of levoglucosan to LGO in the absence of water (FIG. 7A) and in the presence of 2.7% water (FIG. 7B). FIGS. 8A and 8B show the results of the conversion of glucose to LGO in the absence of water (FIG. 8A) and in the presence of 2.7% water (FIG. 8B). FIG. 9 shows the results of the conversion of cellobiose to LGO in the absence of water. In the absence of water, the conversion of LGA was 95% and the yield of LGO was 71% (FIG. 7A). The other detectable product was HMF, which was produced at a 13% yield. Neither glucose nor furfural were detected, suggesting that HMF may be derived mainly from the isomerization of LGO. In contrast, the yield of LGO from LGA was only 31% in the presence of 2.7 wt % water (FIG. 7B). HMF yield increased to 41%. Glucose and furfural were also observed.

A similar result was obtained during glucose dehydration. LGO was formed at 53% yield in the absence of water (FIG. 8A), with LGA formed as an intermediate. The addition of water also increased the HMF yield to 28%, compared with 8% in absence of water (FIG. 8B). The furfural yield was 3-4% regardless of the presence of water.

From the above results, the reaction network shown in Scheme 2 for the dehydration of cellulose to LGO in polar aprotic solvents is proposed. Note that the method is not, however, limited to any underlying mechanism or reaction pathway. Proposed are two competitive routes for cellulose decomposition. One route is the depolymerization reaction that occurs in the absence of water, which is analogous to the pyrolytic depolymerization of cellulose to LGA. In this scheme, LGA is the primary product of cellulose depolymerization, which is then further dehydrated to yield LGO. The transformation of LGA into LGO can occur by two pathways. The commonly proposed mechanism involves the double dehydration of LGA. However, this pathway does not explain why isolevoglucosenone was not detected. The second approach, presented by Shafizadeh et al. (supra), involves 1,4:3,6-dianhydro-a-D-glucopyranose (DGP) as an intermediate between LGA and LGO. Such a mechanism successfully predicts the absence of isolevoglucosenone in the pyrolysates and in the present reactions. Despite the lack of detection of DGP or isolevoglucosenone, it is thought that LGO should not be formed directly from LGA, but rather from an intermediate such as DGP. Under anhydrous condition, the isomerization of LGO into HMF is low.

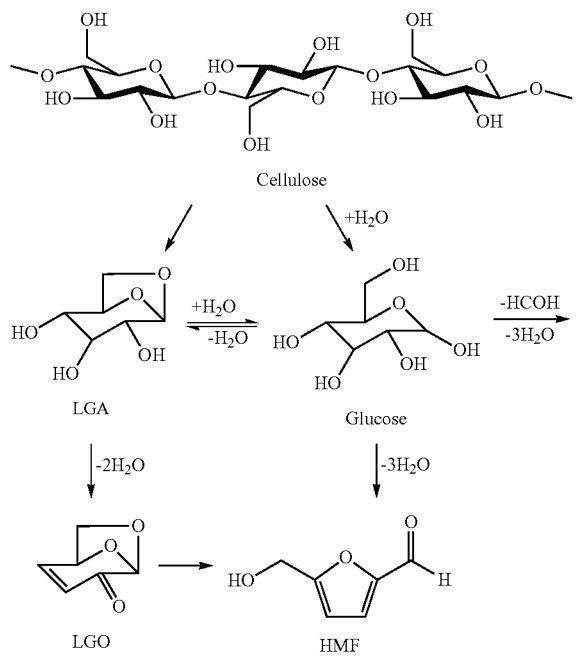

Scheme 3. The possible reaction pathway of cellulose into LGO in THF

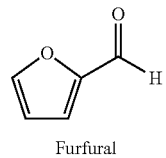

Furfural

The second route for cellulose conversion follows the conventional cellulose hydrolysis pathway. As expected, glucose is the primary product of cellulose hydrolysis in aqueous medium, and it can quickly undergo isomerization and dehydration with acid catalysts to yield HMF. LGA and glucose may also be interconverted via dehydration and hydrolysis. Although Kawamoto has reported that adding water could increase the conversion of LGO to furfural, it is thought that furfural comes from glucose by the tautomerization and retroaldol reaction.

The final product distribution can be tuned by adjusting the water content in the reaction medium. Without water, the main products are LGO and LGA, with small amounts of HMF and furfural also being formed. However, cellulose dehydration was inhibited completely in the presence of small amounts of water, and no anhydrosugars were observed. HMF and furfural were the only products of these reactions. Levulinic acid was also formed in the presence of water, as were insoluble precipitates (humins).

Disclosed is a method to produce LGO and LGA from cellulose under mild reaction conditions (170-230° C.; 5-20 mM $H_2SO_4$) using polar, aprotic solvents. THF is the best solvent tested for this reaction, obtaining a maximum LGO yield of 95% from 1 wt % cellulose after 30 min at 210° C. using 7.5 mM $H_2SO_4$ as catalyst. To our knowledge, this yield of LGO is the highest yet reported. The final product distribution can be controlled by the addition of water to the reaction medium. HMF gradually replaces LGO as the main product with increasing water content.

Reaction Studies:

Reactions were performed in a 100 mL Hastelloy (C-276) autoclave (Parr Instrument Company, series 4560). The vessel and head were dried overnight at 70° C. to remove residual water prior to each reaction. Solutions of cellulose (Avicel® PH-101, moisture content ca. 3 wt %), cellobiose (Sigma Aldrich, purity ≥98%), glucose (Sigma Aldrich, anhydrous), and LGA (Sigma Aldrich, purity 99%), THF (Sigma Aldrich, anhydrous, 99.9%, inhibitor free), and sulfuric acid (Fisher Chemical, A300-500) were sealed in the autoclave following which the vessel was purged five times with helium (Airgas). Zero time was defined as the point at which the heating was started, except where noted. The vessel was then heated to the desired reaction temperature and pressurized to a final pressure of 6.9 MPa. The stirring rate was maintained 600 rpm. The temperature and stirring were controlled by a Parr 4848 Controller. Samples were periodically withdrawn through a dip tube. The reactor was repressurized with helium after withdrawing each sample. The samples were immediately quenched in an ice water bath and filtered with a 0.2 μm syringe filter (IC Millex®-LG, part no. SLLGC13NL). Samples were diluted twice with water prior to analysis.

Determination of Products:

LGO (standards purchased from GlycoSyn, purity 98%) and HMF (standards purchased from Sigma Aldrich, purity ≥98%) were analyzed using a gas chromatograph (Shimadzu, GC-2010 equipped with a flame ionization detector and a Restek RTX-VMS capillary column). The injection port and the detector were held at 240° C. The column flow rate was 0.43 mL min$^{-1}$ with a He carrier gas. The GC oven temperature was initially held at 40° C. for 5 min, ramped to 240° C. at 7.5° C. min$^{-1}$, and kept at 240° C. for 15 min. LGA, glucose and furfural were analyzed using a high-performance liquid chromatograph (HPLC; Shimadzu, LC-20AT) equipped with UV (UV-Vis; SPD-20AV) and RI (RID-10A) detectors. Separation was achieved using a Biorad Aminex HPX-87H column at 30° C. with 5 mM $H_2SO_4$ as the mobile phase, flowing at a rate of 0.6 mL min$^{-1}$. For each analysis, the injection volume was 1 uL.

All yields were calculated as follows:

$$[\text{Yield}]_i (\%) = 100 \times \frac{\text{moles of carbon of product } i}{\text{initial moles of carbon in feed}}$$

Total yield (%) =

$$100 \times \frac{\text{total moles of carbon from all detectable products*}}{\text{initial moles of carbon in feed}}$$

*Detectable products: glucose, levoglucosan, levoglucosenone, HMF and furfural

What is claimed is:

1. A method to produce levoglucosenone (LGO), the method comprising:
   reacting a reactant comprising cellulose, lignocellulose, cellobiose, glucose, or a combination thereof, in a reaction mixture comprising a polar, aprotic solvent and an acid, for a time, at a temperature, and at a hydrogen ion concentration wherein at least a portion of the cellulose, lignocellulose, cellobiose, or glucose present in the reactant is converted to LGO.

2. The method of claim 1, wherein the acid is present in an amount to yield a hydrogen ion concentration in the reaction mixture of from about 5 mM to about 500 mM.

3. The method of claim 1, wherein the acid is present in an amount to yield a hydrogen ion concentration in the reaction mixture of from about 5 mM to about 100 mM.

4. The method of claim 1, wherein the acid is present in an amount to yield a hydrogen ion concentration in the reaction mixture of from about 5 mM to about 50 mM.

5. The method of claim 1, wherein the acid is a Brønsted-Lowry Acid.

6. The method of claim 1, wherein the acid is a mineral acid.

7. The method of claim 1, wherein the temperature is from about 80° C. to about 500° C.

8. The method of claim 1, wherein the temperature is from about 80° C. to about 400° C.

9. The method of claim 1, wherein the temperature is from about 80° C. to about 300° C.

10. The method of claim 1, wherein the temperature is from about 140° C. to about 250° C.

11. The method of claim 1, wherein the polar, aprotic solvent is selected from the group consisting of beta-, gamma-, and delta-lactones, hydrofurans, hydropyrans, dihydrolevoglucosenone, 6,8-dioxabicyclo-octane, and combinations thereof.

12. The method of claim 1, wherein the polar, aprotic solvent is selected from the group consisting of dichloromethane, tetrahydrofuran, ethylacetate, acetone, dimethylformamide, acetonitrile, dimethylsulfoxide, propylene carbonate, N-methyl-2-pyrrolidone, dihydrolevoglucosenone, 6,8-dioxabicyclo-octane, and hexamethylphosphoramide.

13. The method of claim 1, wherein the reaction mixture comprises no more than about 2.0 wt % water at any time during the reaction.

14. A method to produce levoglucosenone (LGO), the method comprising:
   reacting a reactant comprising cellulose, lignocellulose, cellobiose, glucose, or a combination thereof, in a reaction mixture comprising a polar, aprotic solvent and an acid, for a time, at a temperature, and at a hydrogen ion concentration wherein at least a portion of the cellulose or lignocellulose present in the reactant is converted to LGO; and
   wherein the reaction mixture comprises no more than about 2.0 wt % water at any time during the reaction.

15. The method of claim 14, wherein the acid is present in an amount to yield a hydrogen ion concentration in the reaction mixture of from about 5 mM to about 500 mM.

16. The method of claim 14, wherein the acid is present in an amount to yield a hydrogen ion concentration in the reaction mixture of from about 5 mM to about 100 mM.

17. The method of claim 14, wherein the acid is present in an amount to yield a hydrogen ion concentration in the reaction mixture of from about 5 mM to about 50 mM.

18. The method of claim 14, wherein the acid is a Brønsted-Lowry acid.

19. The method of claim 14, wherein the acid is a mineral acid.

20. The method of claim 14, wherein the temperature is from about 80° C. to about 300° C.

21. The method of claim 14, wherein the temperature is from about 80° C. to about 500° C.

22. The method of claim 14, wherein the temperature is from about 80° C. to about 400° C.

23. The method of claim 14, wherein the temperature is from about 140° C. to about 250° C.

24. The method of claim 14, wherein the polar, aprotic solvent is selected from the group consisting of beta-, gamma-, and delta-lactones, hydrofurans, hydropyrans, dihydrolevoglucosenone, 6,8-dioxabicyclo-octane, and combinations thereof.

25. The method of claim 14, wherein the polar, aprotic solvent is selected from the group consisting of dichloromethane, tetrahydrofuran, ethylacetate, acetone, dimethylformamide, acetonitrile, dimethylsulfoxide, propylene carbonate, N-methyl-2-pyrrolidone, dihydrolevoglucosenone, 6,8-dioxabicyclo-octane, and hexamethylphosphoramide.

26. The method of claim 14, wherein the reaction mixture is initially substantially devoid of water.

27. The method of claim 1, wherein the reaction mixture is initially substantially devoid of water.

* * * * *